United States Patent
Shikata et al.

(10) Patent No.: US 7,399,610 B2
(45) Date of Patent: Jul. 15, 2008

(54) METHOD FOR CELL-FREE PROTEIN SYNTHESIS USING EXTRACT SOLUTION DERIVED FROM INSECT CELL

(75) Inventors: Masamitsu Shikata, Kyoto (JP); Nobuhiro Hanafusa, Kyoto (JP); Shinichiro Kobayashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/247,294

(22) Filed: Oct. 12, 2005

(65) Prior Publication Data

US 2006/0084146 A1    Apr. 20, 2006

(30) Foreign Application Priority Data

Oct. 15, 2004    (JP)    ............... 2004-302062

(51) Int. Cl.
   *C12P 21/06*    (2006.01)
(52) U.S. Cl. .................................... 435/68.1
(58) Field of Classification Search ............... 435/68.1
   See application file for complete search history.

(56) References Cited

U.S. PATENT DOCUMENTS 5,478,730 A * 12/1995 Alakhov et al. ............ 435/68.1
2003/0157594 A1    8/2003    Hara et al.
2004/0191858 A1    9/2004    Ezure et al.

FOREIGN PATENT DOCUMENTS

| JP | 7-110236 | 11/1995 |
|---|---|---|
| JP | 2000-325076 A | 11/2000 |
| JP | 2002-539840 | 11/2002 |
| JP | 2004-215651 A | 8/2004 |
| WO | WO 00/58493 | 10/2000 |

OTHER PUBLICATIONS

Alexander S. Spirin, et al., "A Continuous Cell-Free Translation System Capable of Producing Polypeptides in High Yield", Science, vol. 242, Nov. 25, 1988, pp. 1162-1164.

* cited by examiner

*Primary Examiner*—Karen Cochrane Carlson
*Assistant Examiner*—Agnes B. Rooke
(74) *Attorney, Agent, or Firm*—Cheng Law Group PLLC

(57) ABSTRACT

The present invention provides a simple cell-free protein synthesis method capable of affording synthesis of a protein in a high amount in a short time at a low cost. A method for cell-free protein synthesis using an extract derived from an insect cell, the method comprising removing a component which can pass through a semipermeable membrane through the semipermeable membrane while maintaining synthesis reaction, thereby to continuously synthesize a protein. Preferably, an mRNA is additionally supplied while said synthesis reaction is maintained. Further, said insect cell is preferably an established culture cell derived from *Trichoplusia ni* ovum cell.

17 Claims, 1 Drawing Sheet

METHOD FOR CELL-FREE PROTEIN SYNTHESIS USING EXTRACT SOLUTION DERIVED FROM INSECT CELL

BACKGROUND OF THE INVENTION

1. Field of the Invention

The present invention relates to a method for cell-free protein synthesis. More specifically, the present invention relates to a synthesis method capable of improving an amount of synthesized protein per unit time with a simple method.

2. Disclosure of the Related Art

In recent years, genetic information of many organisms, such as human genome, has been decoded. Under the circumstances, functional analysis of proteins and creation of genomic medicine based on such genetic information have been attracting attention for postgenomic studies. Application and utilization of proteins corresponding to such genetic information for pharmaceutical products and the like requires easy synthesis of extensive kinds of proteins in a short time.

At present, expression systems using viable cells (hereinafter sometimes to be referred to as "cell-system") of yeast, insect cell and the like by the gene recombination technique have been widely utilized as the production methods of proteins. However, viable cells show a propensity toward elimination of exogenous proteins for their functional retention, and there are many proteins that cannot be expressed easily since expression of cytotoxic proteins in viable cells prevents cell growth.

On the other hand, as a production method of protein free of a cell-system, cell-free protein synthesis has been known, which includes adding a substrate, an enzyme and the like to a cell rupture, extract solution and the like to provide a wide choice of genetic information translation systems of organisms in test tubes, and reconstructing a synthetic system capable of linking the necessary number of amino acid residues in a desired order using an mRNA encoding an object protein. Such a cell-free protein synthesis is relatively free of the limitation imposed on the above-mentioned cell-system protein synthesis, and is capable of synthesizing proteins without killing the organism. In addition, because the production of protein does not accompany operations of culture and the like, the protein can be synthesized in a short time as compared to cell-systems. Moreover, inasmuch as the cell-free protein synthesis also affords a large scale production of proteins consisting of amino acid sequences not utilized by the organism, it is expected to be a promising expression method. However, a cell-free protein synthesis system has a problem in that reaction time is shorter and the amount of a synthesized protein is extremely smaller as compared to a cell-system. In order to overcome such a problem of a batch method which is a conventional cell-free protein synthesis method, various studies have been carried out.

For example, there has been reported that a protein can be continuously synthesized by a method of feeding a reaction solution to an ultrafilter (flow method) in A. S. Spirin et al., Science, 242, 1162-1164 (1988) or JP-B-07-110236. However, such a flow method requires large-scale devices, and is therefore disadvantageous in terms of cost.

JP-A-2002-539840 describes a cell-free protein synthesis method by a method of using a dialyzer (dialysis method). In this method, a wheat germ extract is used to synthesize CAT by means of a translation system or a coupled transcription/translation system. Further, $Mg^+$ and NTP concentrations are continuously changed during synthesis to improve the yield of CAT. However, in the case of a translation system, the yield of CAT obtained by this method is about 17 µg/mL. On the other hand, in the case of a coupled transcription/translation system in which $Mg^+$ and NTP concentrations are continuously changed, the yield of CAT obtained by this method is 32 µg/mL at best.

Further, on the other hand, as a cell rupture or extract solution to be applied to the cell-free protein synthesis, use of various substances of biological derivation has been considered and investigations are underway. Of such substances, since insect cells do not require, unlike many mammalian culture cells, culture under a carbon dioxide atmosphere, can be cultured in a serum-free medium, and can express in a large amount in a cell-system while retaining the inherent biological activity with posttranslational modification, they are used for the expression of various proteins. If the insect cell can be used for a cell-free system, posttranslational modification, such as glycosylation and the like, is fully expected to be applicable. Thus, the development of utilization of the insect cell is drawing attention.

As a method for preparing an extract solution for cell-free protein synthesis, a method of extraction from an insect cell has been disclosed in JP-A-2000-325076, JP-A-2004-215651, or the like. JP-A-2000-325076 discloses a method for reducing a pressure applied to an insect cell after pressurization in an inert gas atmosphere, thereby to rupture the insect cell to allow for extraction. JP-A-2004-215651/discloses, as a method for easily preparing an insect cell extract solution which affords synthesis of a large amount of protein, a method for preparing an insect cell extraction solution for cell-free protein synthesis, the method comprising at least a step of rapidly freezing an insect cell suspended in a solution for extraction. In addition, JP-A-2004-215651 also discloses a method for cell-free protein synthesis in accordance with a batch method, using the insect cell extract solution prepared as described above.

SUMMARY OF THE INVENTION

It is therefore an object of the present invention to provide a simple cell-free protein synthesis method capable of affording synthesis of a protein in a high amount in a short time at a low cost.

The present invention comprises the followings:

(1) A method for cell-free protein synthesis using an extract derived from an insect cell, the method comprising removing a component which can pass through a semipermeable membrane through the semipermeable membrane while maintaining synthesis reaction, thereby to continuously synthesize a protein.

(2) The cell-free protein synthesis method according to the above-mentioned (1), wherein mRNA is additionally supplied while said synthesis reaction is maintained.

(3) The cell-free protein synthesis method according to the above-mentioned (2), wherein said mRNA to be additionally supplied is used in the form of an aqueous solution containing mRNA in a proportion of 5 µg/µL-50 µg/µL.

(4) The cell-free protein synthesis method according to the above-mentioned (2), wherein said mRNA is additionally supplied to the reaction solution in such a manner that newly added mRNA is contained in the reaction solution in a proportion of 5 µg/mL-2,000 µg/mL.

(5) The cell-free protein synthesis method according to any of the above-mentioned (1)-(4), wherein said component which can pass through the semipermeable membrane includes a degradation product formed during synthesis.

(6) The cell-free protein synthesis method according to any of the above-mentioned (1)-(5), wherein said semipermeable membrane is selected from the group consisting of a dialysis membrane, an ultrafiltration membrane, an ultrafiltration barrier, and a membrane which can chemically or biologically trap target substance.

(7) The cell-free protein synthesis method according to any of the above-mentioned (1)-(6), herein said insect cell is an established culture cell derived from *Trichoplusia ni* ovum cell.

According to the present invention, it is possible to provide a cell-free protein synthesis method capable of affording synthesis of a protein in a high amount in a short time at a low cost.

DETAILED DESCRIPTION OF THE INVENTION

Figure 1:
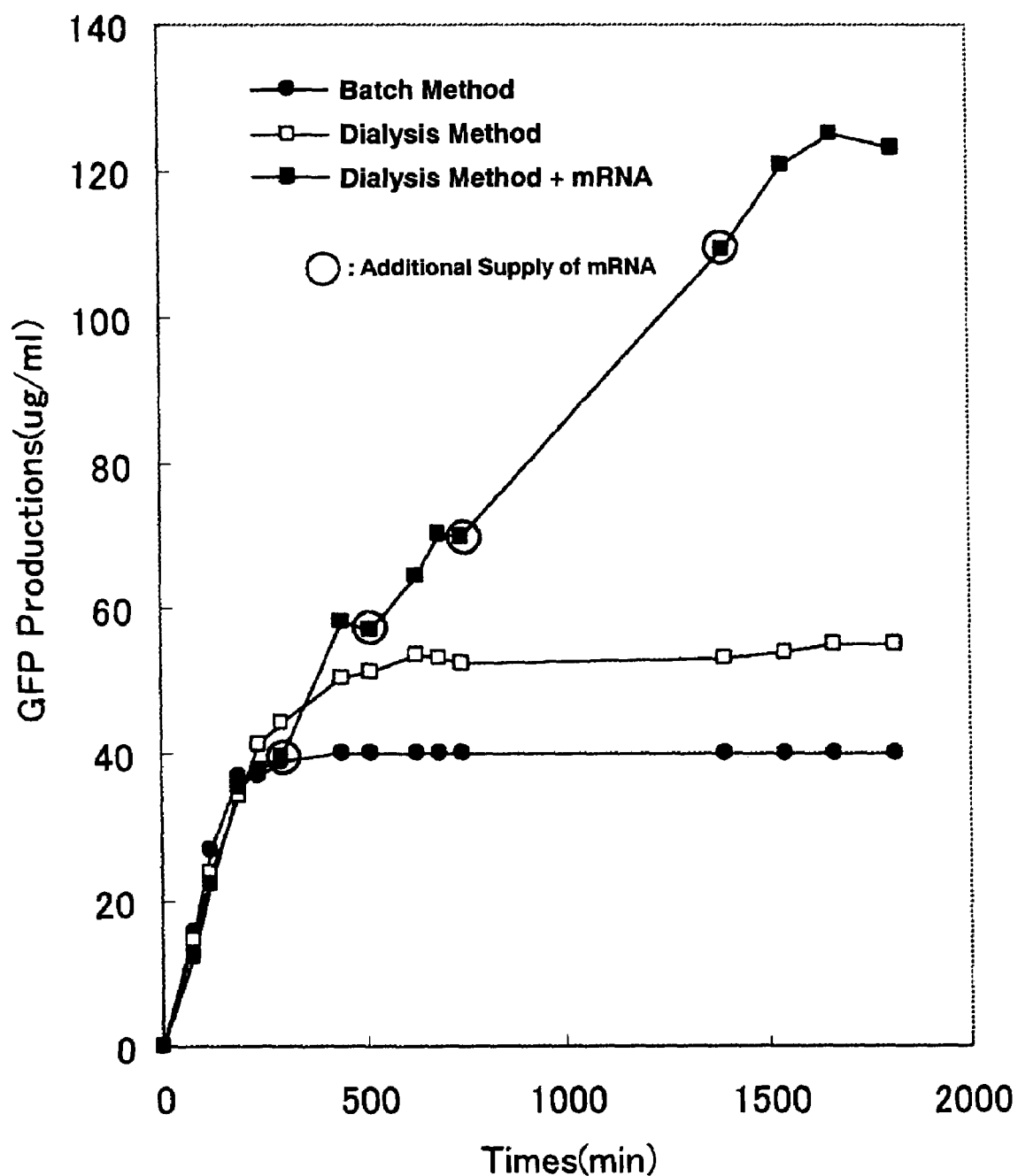
FIG. 1 is a graph showing the result of protein synthesis carried out by a conventional method (batch method) and the results of protein synthesis carried out by methods according to the present invention (dialysis method and dialysis method+mRNA).

The present invention provides a cell-free protein synthesis method using an extract derived from an insect cell, comprising removing a component which can pass through a semi-permeable membrane during synthesis reaction, thereby to continuously synthesize a protein. In the present specification, the "protein" encompasses oligopeptide and polypeptide.

The insect cell is not subject to any particular imitation, and, for example, cells derived from insects of Lepidoptera, Orthoptera, Diptera, Hymenoptera, Coleoptera, Neuroptera, Hemiptera and the like can be used. Of these, cells derived from insects of Lepidoptera, Hemiptera and the like are preferable, because many culture cell lines thereof have been established. Furthermore, the insect cell in the present invention may be a cell derived from any tissue, and, for example, blood cell, gonad-derived cell, fat body-derived cell, embryo-derived cell, hatch larva-derived cell and the like can be used without any particular limitation. Of these, gonad-derived cell, which is considered to have high protein production capability, is preferably used. Particularly, use of High Five (manufactured by Invitrogen), which is a cell derived from the ovum of *Trichoplusia ni* or Sf21 (manufactured by Invitrogen), which is a cell derived from *Spodoptera frugiperda* ovary cell, as an insect cell is preferable, because they have high protein synthesis ability in a cell-system and can be cultured in a serum-free medium.

In the present invention, the cell is not limited to an insect cell derived from a single tissue of a single species of insect, and it may be derived from plural kinds of tissues of a single species of insect, a single tissue of plural species of insects, or plural kinds of tissues of plural species of insects.

In the present invention, a preparation method of an insect cell extract solution to be used for a cell-free protein synthesis system is not particularly limited. For example, a method disclosed in JP-A-2004-215651, that is, a method for rapidly freezing an insect cell suspended in a solution for extraction, thereby to rupture the insect cell to allow for extraction can be used. This method is preferably used for the following reasons: cells can be ruptured under mild conditions, so that components essential for cell-free protein synthesis can be taken out from the cells without damage; contamination with RNase and the like from the tools and the like can be prevented; and incorporation of a substance inhibiting translation reaction which is of concern in the case of cell rupture using a reagent such as a surfactant and the like can be avoided.

Specifically, the insect cell extract solution is prepared in the form of an aqueous solution containing 1 mg/mL-200 mg/mL, preferably 10 mg/mL-100 mg/mL of a protein in a protein concentration, together with 10 mM-500 mM, preferably 50 mM-300 mM of potassium acetate, 0.1 mM-10 mM, preferably 0.5 mM-5 mM of magnesium acetate, 0.1 mM-10 mM, preferably 0.5 mM-5 mM of dithiothreitol (hereinafter sometimes to be referred to as "DTT"), 1 µM-50 mM, preferably 0.01 mM-5 mM of PMSF, and 5 mM-200 mM, preferably 10 mM-100 mM of HEPES-KOH (pH 4-10, preferably 6.5-8.5). Preferably, such an insect cell extract solution is subjected to nuclease treatment.

In a method for cell-free protein synthesis of the present invention, a reaction solution prepared by adding additives necessary for protein synthesis in a cell-free system to the above-mentioned insect cell extract solution is generally used. The above-mentioned additive is not particularly limited and any additive can be used as long as it is conventionally used in the field of protein synthesis in a cell-free system.

The above-mentioned reaction solution is preferably prepared in such a manner that the insect cell extract solution is contained in a proportion of 10 (v/v)%-80 (v/v)%, particularly 30 (v/v)%-60 (v/v)%. In other words, it is preferably prepared in such a manner that the content of the extract derived from insect cells is 0.1 mg/mL-160 mg/mL, more preferably 3 mg/mL-60 mg/mL in a protein concentration, throughout the above-mentioned reaction solution. When the content of the extract is less than 0.1 mg/mL or above 160 mg/mL in a protein concentration, the synthesis rate of the object protein may become lower.

Generally, the above-mentioned reaction solution contains, as components other than the insect cell extract solution, at least potassium salt, magnesium salt, DTT, adenosine triphosphate, guanosine triphosphate, creatine phosphate, creatine kinase, amino acid component, RNase inhibitor, tRNA, exogenous mRNA and buffer. This advantageously realizes a reaction solution for cell-free protein synthesis, which is further capable of synthesizing a large amount of protein in a short time.

The potassium salt in the reaction solution is free of any particular limitation as long as it does not inhibit the action of the present invention, and can be used in a general form, such as potassium acetate, potassium carbonate, potassium hydrogen carbonate, potassium chloride, dipotassium hydrogenphosphate, dipotassium hydrogen citrate, potassium sulfate, potassium dihydrogenphosphate, potassium iodide, potassium phthalate and the like, with preference given to potassium acetate. Potassium salt acts as a cofactor in the protein synthesis reaction.

The content of potassium salt in the reaction solution is free of any particular limitation, but from the aspect of preservation stability, it is preferably 10 mM-500 mM, more preferably 50 mM-150 mM, in the reaction solution, in the case of a monovalent potassium salt, such as potassium acetate and the like. When the content of the potassium salt is less than 10 mM or more than 500 mM, the components essential for protein synthesis tend to become unstable.

The above-mentioned magnesium salt is free of any particular limitation as long as it does not inhibit the action of the present invention, and can be used in a general form such as magnesium acetate, magnesium sulfate, magnesium chloride, magnesium citrate, magnesium hydrogen phosphate, magnesium iodide, magnesium lactate, magnesium nitrate, magnesium oxalate and the like, with preference given to magnesium acetate. Magnesium salt also acts as a cofactor in the protein synthesis reaction.

The content of the magnesium salt in the reaction solution is free of any particular limitation, but from the aspect of preservation stability, it is preferably 0.1 mM-10 mM, more preferably 0.5 mM-3 mM, in the reaction solution, in the case of a divalent salt, such as magnesium acetate and the like. When the content of magnesium salt is less than 0.1 mM or more than 10 mM, the components essential for protein synthesis tend to become unstable.

The above-mentioned DTT is added for prevention of oxidization, and is preferably contained in an amount of 0.1 mM-10 mM, more preferably 0.2 mM-5 mM, in the reaction solution. When the content of DTT is less than 0.1 mM or more than 10 mM, the components essential for protein synthesis tend to become unstable.

The adenosine triphosphate (hereinafter sometimes to be referred to as "ATP") in the reaction solution is preferably contained in the reaction solution in a proportion of 0.01 mM-10 mM, more preferably 0.1 mM-5 mM, in view of the rate of protein synthesis. When ATP is contained in a proportion of less than 0.01 mM or above 10 mM, the synthesis rate of the protein tends to become lower.

The guanosine triphosphate (hereinafter sometimes to be referred to as "GTP") in the reaction solution preferably contained in the reaction solution in a proportion of 0.01 mM-10 mM, more preferably 0.05 mM-5 mM, in view of the rate of protein synthesis. When GTP is contained in a proportion of less than 0.01 mM or above 10 mM, the synthesis rate of the protein tends to become lower.

The creatine phosphate in the reaction solution is a component for continuous synthesis of protein and added for regeneration of ATP and GTP. The creatine phosphate is preferably contained in the reaction solution in a proportion of 1 mM-200 mM, more preferably 10 mM-100 mM, in view of the rate of protein synthesis. When creatine phosphate is contained in a proportion of less than 1 mM, sufficient amounts of ATP and GTP may not be regenerated easily. As a result, the rate of protein synthesis tends to become lower. When the creatine phosphate content exceeds 200 mM, it acts as an inhibitory substance and the rate of protein synthesis tends to become lower.

The creatine kinase in the reaction solution is a component for continuous synthesis of protein and added along with creatine phosphate for regeneration of ATP and GTP. The creatine kinase is preferably contained in the reaction solution in a proportion of 1 µg/mL-1000 µg/mL, more preferably 10 µg/mL-500 µg/mL, in view of the rate of protein synthesis. When the creatine kinase content is less than 1 µg/mL, sufficient amount of ATP and GTP may not be regenerated easily. As a result, the rate of protein synthesis tends to become lower. When the creatine kinase content exceeds 1000 µg/mL, it acts as an inhibitory substance and the synthesis rate of the protein tends to become lower.

The amino acid component in the reaction solution contains at least 20 kinds of amino acids, i.e., valine, methionine, glutamic acid, alanine, leucine, phenylalanine, glycine, proline, isoleucine, tryptophan, asparagine, serine, threonine, histidine, aspartic acid, tyrosine, lysine, glutamine, cystine and arginine. This amino acid includes radioisotope-labeled amino acid. Where necessary, modified amino acid may be contained. The amino acid component generally contains almost the same amount of various kinds of amino acids.

In the present invention, the above-mentioned amino acid component is preferably contained in the reaction solution in a proportion of 1 µM-1000 µM, more preferably 10 µM-200 µM, in view of the rate of protein synthesis. When the amount of the amino acid component is less than 1 µM or above 1000 µM, the synthesis rate of the protein tends to become lower.

The RNase inhibitor in the reaction solution is added to prevent RNase, which is derived from insect cells contaminating the extract solution, from undesirably digesting mRNA and tRNA, thereby preventing synthesis of protein, during cell-free protein synthesis of the present invention. It is preferably contained in the reaction solution in a proportion of 0.1 U/µL-100 U/µL, more preferably 1 U/µL-10 U/µL. When the amount of RNase inhibitor is less than 0.1 U/µL, the degradation activity of RNase often cannot be suppressed sufficiently, and when the amount of the RNase inhibitor exceeds 100 U/µL, protein synthesis reaction tends to be inhibited.

As regards the exogenous mRNA in the reaction solution, a protein (including peptide) to be encoded thereby is not particularly limited as long as the mRNA is not derived from an insect cell, and the mRNA may encode a toxic protein or a glycoprotein. Wether the mRNA contained in the reaction solutin is an exogenous mRNA or mRNA derived from an insect cell can be determined by isolating and purifying the mRNA from an extract solution, synthesizing cDNA using a reverse transcriptase, analyzing abase sequence of the obtained cDNA and comparing the base sequences with the base sequences of known exogenous mRNAs.

The exogenous mRNA to be used is not particularly limited as regards the number of bases and all the exogenous mRNAs may not have the same number of bases as long as they can synthesize the object protein. In addition, as long as the sequences are homologous to the degree allowing synthesis of the object protein, plural bases of each exogenous mRNA may be deleted, substituted, inserted or added.

The exogenous mRNA to be used for the present invention may be a commercially available one or an mRNA obtained by inserting ORF (Open reading frame) of the object protein into the downstream of the 5'-β-globin leader sequence of a commercially available vector, such as pTnT Vector (manufactured by Promega), and performing a transcription reaction using the resulting vector. Furthermore, an exogenous mRNA having a cap structure resulting from the addition of methylated ribonucleotide and the like during transcription reaction may be used.

In the reaction solution, the exogenous mRNA (hereinafter sometimes to be referred to as "mRNA") is preferably contained in a proportion of 5 µg/mL-2000 µg/mL, more preferably 20 µg/mL-1000 µg/mL, in view of the rate of the protein synthesis. When mRNA is less than 5 µg/mL or more than 2000 µg/mL, the rate of the protein synthesis tends to become lower.

The tRNA in the reaction solution contains almost the same amount of each of the tRNAs corresponding to the above-mentioned 20 kinds of amino acids. In the present invention, tRNA is preferably contained in the reaction solution in a proportion of 1 µg/mL-1000 µg/mL, more preferably 10 µg/mL-500 µg/mL, in view of the rate of protein synthesis. When the amount of tRNA is less than 1 µg/mL or exceeds 1000 µg/mL, the rate of protein synthesis tends to become lower.

The above-mentioned buffer imparts a buffer capacity to a reaction solution, and is added for prevention of denaturation of an extract and/or reaction product caused by radical change in pH of the reaction solution due to, for example, the addition of an acidic or basic substance and the like. Such buffer is free of any particular limitation, and, for example, HEPES-KOH, Tris-HCl, acetic acid-sodium acetate, citric acid-sodium citrate, phosphoric acid, boric acid, MES, PIPES and the like can be used.

The buffer is preferably one that maintains the pH of the reaction solution at 4-10, more preferably 6.5-8.5. When the pH of reaction solution is less than 4 or more than 10, the components essential for the reaction of the present invention may be denatured. From this aspect, the use of HEPES-KOH (pH 6.5-8.5) is particularly preferable among the above-mentioned buffers.

While the content of the buffer in reaction solution is free of any particular limitation, it is preferably 5 mM-200 mM, more preferably 10 mM-50 mM, to maintain preferable buffer capacity. When the content of the buffer is less than 5 mM, the pH tends to change radically due to the addition of an acidic or basic substance, which in turn may cause denaturation of the extract and/or reaction product, and when the content of the buffer exceeds 200 mM, the salt concentration becomes too high and the components essential for protein synthesis tend to become unstable.

Moreover, the above-mentioned reaction solution preferably contains EGTA. When EGTA is contained, EGTA forms chelate with a metal ion in the extract solution to inactivate ribonuclease, protease and the like. This in turn inhibits decomposition of the components essential for protein synthesis of the present invention. Even when a nuclease treatment is applied to an extract solution as mentioned above, an adverse influence of nuclease on the cell-free protein synthesis can be certainly prevented because the reaction solution contains EGTA. EGTA is preferably contained in the above-mentioned reaction solution at 0.01 mM-50 mM, more preferably 0.1 mM-10 mM, in view of preferable exertion of the above-mentioned decomposition inhibitory ability. When EGTA is contained in less than 0.01 mM, decomposition activity of essential components cannot be sufficiently suppressed. When it exceeds 50 mM, it tends to inhibit protein synthesis reaction.

In other words, the reaction solution to be used for the cell-free protein synthesis method of the present invention is preferably made in the form of an aqueous solution to contain the above-mentioned extract solution in a proportion of 30 (v/v)%-60 (v/v)%, together with 50 mM-150 mM of potassium acetate, 0.5 mM-3 mM of magnesium acetate, 0.2 mM-5 mM of DTT, 0.1 mM-5 mM of ATP, 0.05 mM-5 mM of GTP, 10 mM-100 mM of creatine phosphate, 10 μg/mL-500 μg/mL of creatine kinase, 10 μM-200 μM of amino acid component, 1 U/μL-10 U/μL of RNase inhibitor, 10 μg/mL-500 μg/mL of tRNA, 20 μg/mL-1000 μg/mL of exogenous mRNA and 10 mM-50 mM of HEPES-KOH (pH 6.5-8.5). In addition, the reaction solution is more preferably made to contain 0.1 mM-10 mM of EGTA in addition to the above.

In the cell-free protein synthesis method according to the present invention, the reaction solution as described above is prepared, and then synthesis is initiated at an appropriate reaction temperature. The reaction solution is brought into contact with an external solution through a semipermeable membrane. In this regard, any form may be employed as long as a reaction solution is brought into contact with an external solution through a semipermeable membrane. Examples of such a form include: a form that a reaction solution received in a semipermeable membrane is immersed in a reaction chamber receiving an external solution; a form that a first reaction chamber having a structure in which a reaction solution is received in a vessel having a semipermeable membrane on its bottom is immersed in a second reaction chamber receiving an external solution; a form that a chamber of a reaction solution and a chamber of an external solution are stacked with a semipermeable membrane interposed therebetween and received in a reaction bath; and the like. According to such a mechanism using a semipermeable membrane, a component which can pass through the semipermeable membrane is removed from a reaction solution through the semipermeable membrane and is transferred into an external solution while synthesis reaction is maintained.

The semipermeable membrane is not particularly limited, and various well-known membranes may be used. Examples of such a semipermeable membrane include a dialysis membrane, an ultrafiltration membrane, an ultrafiltration barrier, and a membrane which can chemically or biologically trap a target substance. These membranes are different in their pore size, respectively, and therefore a membrane to be used can be appropriately selected depending on the kind of substance to be passed through a membrane. Preferably, a membrane capable of removing a substance having a molecular weight of 3,000 or less, particularly 10,000 or less from a reaction solution and transferring the removed substance into an external solution is used.

Specific examples of a component which can pass through a semipermeable membrane include degradation products formed during synthesis, that is, ADP, AMP, GDP, GMP, phosphates, pyrophosphates and the like. These components are substances inhibiting protein synthesis. According to the method of the present invention, these components are removed from the reaction solution through the semipermeable membrane and are then transferred into the external solution while a cell-free synthesis system is maintained. By carrying out such a removing operation, it is possible to more continuously and efficiently carry out cell-free protein synthesis for a long time. In some cases, a component which can pass through a semipermeable membrane includes a relatively small synthesized protein.

The external solution to be used in the present invention is not particularly limited as long as it has composition capable of receiving the component which can pass through the semipermeable membrane from the reaction solution through the semipermeable membrane, as described above. For example, an external solution having composition obtained by eliminating an extract solution, tRNA, mRNA, creatine kinase, and RNase inhibitor from the aforementioned reaction solution, that is, an external solution having composition containing HEPES-KOH, potassium acetate, magnesium acetate, ATP, GTP, creatine phosphate, DTT, amino acid, and EGTA in the same concentrations as those in the aforementioned reaction solution can be used. By using such an external solution including an energy source necessary for protein synthesis, such as ATP, the aforementioned degradation products and the like are removed from the reaction solution and transferred into the external solution and, also, the energy source is supplied from the external solution to the reaction solution. As a result, there is an advantage of extension of reaction time for protein synthesis.

Among the aforementioned membranes, in the present invention, a dialysis membrane is preferably used as a semipermeable membrane to carry out protein synthesis while dialyzing the reaction solution.

The reaction temperature is generally within the range of 10° C.-40° C., preferably 15° C.-30° C. When the reaction temperature is lower than 10° C., the synthesis rate of the protein tends to become lower, and when the reaction temperature exceeds 40° C., the essential components tend to be denatured.

In the present invention, preferably, mRNA is additionally supplied to the reaction solution while a synthesis reaction is maintained. The mRNA to be additionally supplied is preferably used in the form of an aqueous solution containing mRNA in a proportion of 5 μg/μL-50 μg/μL. When the mRNA content is lower than 5 μg/μL, a total amount of the solution to be added is increased and the volume of the reaction solution per se is also increased. As a result, the composition of the reaction solution tends to be very far from a preferred composition.

Preferably, mRNA is additionally supplied to the reaction solution in such a manner that newly added mRNA is contained in the reaction solution in a proportion of 5 µg/mL-2,000 µg/mL, more preferably 20 µg/mL-1,000 µg/mL. When the content of additionally supplied mRNA is lower than 5 µg/mL or exceeds 2,000 µg/mL, the rate of protein synthesis tends to become lower. By the additional supply of mRNA, it is possible for the reaction solution to always contain a high concentration of mRNA. The cell-free protein synthesis method according to the present invention has an advantage that synthesis reaction can be maintained by additionally supplying mRNA; therefore, the operation of synthesis is simple.

The timing of additional supply of mRNA is not particularly limited, and may be appropriately determined by those skilled in the art. However, mRNA is preferably added at the time when the reaction rate of protein synthesis becomes slow. Although the timing of additional supply of mRNA depends on various factors such as the composition of the extract solution, the composition of the reaction solution, and the amount of mRNA to be additionally supplied, mRNA can be additionally supplied, for example, once every 3-12 hours.

In the present invention, the operation of the above-mentioned additional supply may be automatically controlled. Since the cell-free protein synthesis method according to the present invention is simple, a device for automatic control can also be simplified. The automatic control is preferred in that the operation for synthesis reaction can be reliably carried out and more simplified.

The amount of protein synthesized by the cell-free protein synthesis method of the present invention can be measured by activity assay of enzyme, SDS-PAGE, immunoassay and the like.

The protein synthesized by the cell-free protein synthesis method of the present invention is free of any particular limitation.

EXAMPLES

The present invention is explained in more detail in the following by way of Examples; however, the present invention is not limited thereto.

In Examples 1 and 2, green fluorescent protein (GFP) was synthesized by a dialysis method in a cell-free protein synthesis system using an extract solution derived from High Five (manufactured by Invitrogen) as insect cells.

Example 1

According to the protocol of PROTEIOS (TOYOBO), a pEU-GFP plasmid was constructed by inserting a green fluorescent protein (GFP) gene into the downstream of Ω sequence of a pEU-vector (manufactured by TOYOBO), and then mRNA was synthesized using the circular DNA (it is to be noted that mRNA synthesis can also be carried out by using a PCR product obtained using the circular DNA as a template) According to the protocol of RiboMAX Large Scale RNA Production System (manufactured by Promega), ethanol precipitation and gel filtration were carried out after the completion of mRNA synthesis, and then the amount of synthesized mRNA was measured by ultraviolet absorption spectrometry. The obtained mRNA was used for cell-free protein synthesis. On the other hand, an insect cell extract solution was prepared in the same manner as in Example 1 described in JP-A-2004-215651.

A reaction solution was an aqueous solution having the following composition: 40 mM HEPES-KOH (pH 7.9), 100 mM potassium acetate, 2 mM magnesium acetate, 0.5 mM ATP, 0.25 mM GTP, 20 mM creatine phosphate, 200 µg/mL creatine kinase, 2 mM DTT, 80 µM amino acid (20 kinds), 0.25 mM EGTA, 1 U/µL RNase inhibitor, 200 µg/mL tRNA (derived from brewer's yeast), 50 (v/v)% extract solution, and 320 µg/mL mRNA. The total amount of the reaction solution having such composition was 70 µL (that is, the content of mRNA was 22.4 µg).

An external solution was an aqueous solution having the following composition: 40 mM HEPES-KOH (pH 7.9), 100 mM potassium acetate, 2 mM magnesium acetate, 0.5 mM ATP, 0.25 mM GTP, 20 mM creatine phosphate, 2 mM DTT, 80 µM amino acid (20 kinds), and 0.25 mM EGTA. The total amount of the external solution having such composition was 1,500 µL.

As a dialyzer, a dialysis cup (MWCO: 3500, manufactured by Daiichi Pure Chemicals) was used. 70 µL of the reaction solution was placed in the dialysis cup having a dialysis membrane on its bottom. On the other hand, 1,500 µL of the external solution was placed in a buffer tank. The dialysis cup was immersed in the external solution in the buffer tank in such a manner that the dialysis membrane on the bottom of the dialysis cup was sunk below the surface of the external solution in the buffer tank. Reaction was performed at 25° C.

Example 2

Reaction was performed in the same manner as in Example 1 except that an mRNA solution was newly added after a lapse of 240 minutes, 570 minutes, 745 minutes, and 1,400 minutes from the beginning of the synthesis reaction.

It is to be noted that in Example 2, mRNA to be additionally supplied was used in the form of an aqueous solution containing mRNA in a proportion of 5.1 µg/µL, and such an aqueous solution of mRNA was added in such a manner that a final concentration (that is, the concentration of newly added mRNA in the reaction solution) was 320 µg/mL.

Comparative Example 1

In the Comparative Example 1, reaction was performed by a batch method at 25° C. using 40 µL of a reaction solution obtained in the same manner as in Example 1.

For each of the GFPs synthesized in Examples 1 and 2 and comparative Example 1, fluorescence intensity measurement was carried out using a microplate reader (GENios, manufactured by TECAN). The concentration of the synthesized GFP was determined using a GFP concentration-fluorescence intensity calibration curve prepared by measuring the fluorescence intensity of each dilute solution having a known GFP concentration of a GFP dilution series. FIG. 1 is a graph which shows a comparison of the amount of GFP synthesized by the method of the present invention (Examples 1 and 2) to the amount of GFP synthesized by a conventional method (Comparative Example 1). In FIG. 1, the axis of abscissa shows times (min), and the axis of ordinate shows GFP productions (µg/mL). Further, the result of a conventional method (Comparative Example 1) is represented by a line named "batch method", the result of a dialysis method according to the present invention (Example 1), in which mRNA is not additionally supplied, is represented by a line named "dialysis method", and the result of a dialysis method according to the present invention (Example 2), in which mRNA is additionally supplied, is represented by a line named "dialysis method+mRNA". It is to be noted that in the line graph which shows the result of Example 2, circles represent the timing of additional supply of mRNA. As shown in FIG. 1, the amount of synthesized GFP was increased in either case according to the method of the present invention. Particularly, in the case of a dialysis method in which mRNA was additionally supplied (Example 2), the amount of synthesized GFP was significantly increased and was about three times that of a conventional method (Comparative Example 1).

The aforementioned examples show two specific embodiments of the present invention, but the present invention is not limited thereto and other various embodiments are possible. The aforementioned examples are merely illustrative in all respects and should not be construed as being restrictive. In addition, all modifications and changes that belong to equivalents of claims are considered to fall within the scope of the present invention.

What is claimed is:

1. A method for cell-free protein synthesis, said method comprising:
    contacting a reaction solution comprising an insect cell extract solution and necessary components for protein synthesis with an external solution through a semipermeable membrane, wherein the reaction solution is subjected to translation to produce a protein, and
    maintaining the production of said protein, while (a) supplying exogenous mRNA and (b) removing components from said reaction solution by passing said components through the semipermeable membrane into said external solution, said components comprising substances which inhibit protein synthesis and degradation products which form during protein synthesis,
    wherein the insect cell extract solution is obtained by separating the insect cell extract from an insect cell, said insect cell extract comprising insect cell components essential for protein synthesis,
    wherein the insect cell extract solution is an established culture cell derived from insects of Lepidoptera, Orthoptera, Diptera, Hymenoptera, Coleoptra, Neuroptra, Hemiptera,
    wherein said components removed from the reaction solution comprise one or more compounds selected from the group consisting of adenosine diphosphate (ADP), adenosine monophosphate (AMP), gunanosine 5'-diphosphate (GDP), guanosine 5'-monophosphate (GMP), phosphates, pyrophosphates, and products which are degraded and formed during protein synthesis and
    wherein the necessary components for protein synthesis comprise one or more compounds selected from the group consisting of potassium salt, magnesium salt, dithiothreitol, adenosine triphosphate, guanosine triphosphate, creatine phosphate, creatine kinase, amino acid, RNase inhibitor, tRNA, exogenous mRNA, buffer, and EGTA.

2. The cell-free protein synthesis method according to claim 1, wherein said mRNA to be supplied is in the form of an aqueous solution containing mRNA in a proportion of 5 µg/µL-50 µg/µL.

3. The cell-free protein synthesis method according to claim 1, wherein said mRNA is supplied to the reaction solution in such a manner that newly added mRNA is contained in the reaction solution in a proportion of 5 µg/mL-2,000 µg/mL.

4. The cell-free protein synthesis method according to claim 1, wherein said semipermeable membrane is selected from the group consisting of a dialysis membrane, an ultrafiltration membrane, an ultrafiltration barrier, and a membrane which can chemically or biologically trap a substance from said protein synthesis reaction.

5. The cell-free protein synthesis method according to claim 1, wherein said insect cell is an established culture cell derived from *Trichoplusia ni* ovum cell.

6. The cell-free protein synthesis method according to claim 1, wherein the insect cell extract solution is contained in a proportion of 10 (v/v)%-80 (v/v)% and the content of the insect cells extract separated from insect cells is 0.1 mg/ml-160 mg/ml in a protein concentration.

7. The cell-free protein synthesis method according to claim 1, wherein the necessary components for protein synthesis are present in one or more of the following ranges:
    (a) 10 mM-500 mM of potassium salt,
    (b) 0.1 mM-10 mM of magnesium salt,
    (c) 0.1 mM-10 mM of dithiothreitol,
    (d) 0.01 mM-10 mM of adenosine triphosphate,
    (e) 0.01 mM-10 mM of guanosine triphosphate,
    (f) 1 mM-200 mM of creatine phosphate,
    (g) 1 µg/mL-1000 µg/mL of creatine kinase,
    (h) 1 µM-1000 µM of amino acid,
    (i) 0.1 U/µL-100 U/µL of Rnase inhibitor,
    (j) 1 µg/mL-1000 µg/mL of tRNA,
    (k) 5 µg/mL-2000 µg/mL of exogenous mRNA,
    (l) 5 mM-200 mM of buffer, and
    (m) 0.01 mM-50 mM of EGTA.

8. The cell-free protein synthesis method according to claim 1, wherein the semipermeable membrane removes a substance having a molecular weight of 3,000 or less from said reaction solution.

9. The cell-free protein synthesis method according to claim 1, wherein the cell-free protein synthesis reaction is maintained under a reaction temperature of 10° C.-40° C. and a pH of 4-10.

10. The cell-free protein synthesis method according to claim 1, wherein the insect cell extract solution is subjected to nuclease treatment.

11. The cell-free protein synthesis method according to claim 6, wherein the insect cell extract solution is contained in a proportion of 30 (v/v)%-60 (v/v)% and the content of the insect cells extract separated from insect cells is 3 mg/ml-60 mg/ml in a protein concentration.

12. The cell-free protein synthesis method according to claim 7, wherein the necessary components for protein synthesis are present in one or more of the following ranges;
    (a) 50 mM-150 mM of potassium salt,
    (b) 0.5 mM-3 mM of magnesium salt,
    (c) 0.2 mM-5 mM of dithiothreitol,
    (d) 0.1 mM-5 mM of adenosine triphosphate,
    (e) 0.05 mM-5 mM of guanosine triphosphate,
    (f) 10 mM-100 mM of creatine phosphate,
    (g) 10 µg/mL-500 µg/mL of creatine kinase,
    (h) 10 µM-200 µM of amino acid,
    (i) 1 U/µL-10 U/µL of Rnase inhibitor,
    (j) 10 µg/mL-500 µg/mL of tRNA,
    (k) 20 µg/mL-1000 µg/mL of exogenous mRNA,
    (l) 10 mM-50 mM of buffer, and
    (m) 0.1 mM-10 mM of EGTA.

13. The cell-free protein synthesis method according to claim 1, wherein the external solution comprises one or more compounds selected from the group consisting of potassium salt, magnesium salt, dithiotbreitol, adenosine triphosphate, guanosine triphosphate, creatine phosphate, amino acid, buffer, and EGTA.

14. The cell-free protein synthesis method according to claim 9, wherein the cell-free protein synthesis reaction is maintained under a reaction temperature of 15° C.-30° C. and a pH of 6.5-8.5.

15. The cell-free protein synthesis method according to claim 1, wherein the semipermeable membrane removes a substance having a molecular weight of 10,000 or less from said reaction solution.

16. The cell-free protein synthesis method according to claim 3, wherein said mRNA is additionally supplied to the reaction solution in such a manner that newly added mRNA is contained in the reaction solution in a proportion of 20 µg/mL-1,000 µg/mL.

17. The cell-free protein synthesis method according to claim 1, wherein mRNA is additionally supplied once every 3-12 hours.

\* \* \* \* \*